(12) United States Patent
Weber et al.

(10) Patent No.: US 10,827,916 B2
(45) Date of Patent: Nov. 10, 2020

(54) LED ILLUMINATION MODULE

(71) Applicant: Richard Wolf GmbH, Knittlingen (DE)

(72) Inventors: Bernd Claus Weber, Karlsruhe (DE); Rudolf Heimberger, Oberderdingen (DE); Klaus Schrumpf, Kraichtal-Münzesheim (DE); Martina Detert, Munich (DE); Thomas App, Zaisenhausen (DE)

(73) Assignee: RICHARD WOLF GMBH, Knittlingen (DE)

( * ) Notice: Subject to any disclaimer, the term of this patent is extended or adjusted under 35 U.S.C. 154(b) by 344 days.

(21) Appl. No.: 14/765,443

(22) PCT Filed: Jan. 7, 2014

(86) PCT No.: PCT/EP2014/050130
§ 371 (c)(1),
(2) Date: Aug. 3, 2015

(87) PCT Pub. No.: WO2014/121960
PCT Pub. Date: Aug. 14, 2014

(65) Prior Publication Data
US 2016/0000309 A1    Jan. 7, 2016

(30) Foreign Application Priority Data

Feb. 5, 2013   (DE) .................. 10 2013 201 808

(51) Int. Cl.
*A61B 1/00*       (2006.01)
*A61B 1/06*       (2006.01)
(Continued)

(52) U.S. Cl.
CPC ........ *A61B 1/0684* (2013.01); *A61B 1/00114* (2013.01); *A61B 1/0676* (2013.01);
(Continued)

(58) Field of Classification Search
CPC ..... F21V 23/06; H01R 2201/12; H01R 24/38; A61B 1/0684; A61B 1/00114;
(Continued)

(56) References Cited

U.S. PATENT DOCUMENTS 6,492,725 B1   12/2002   Loh et al.
7,284,896 B2   10/2007   Wu
(Continued)

FOREIGN PATENT DOCUMENTS

EP    2 287 524 A1    2/2011
EP    2 311 366 A1    4/2011
JP    2011-083617 A   4/2011

*Primary Examiner* — Timothy J Neal
(74) *Attorney, Agent, or Firm* — McGlew and Tuttle, P.C.

(57) ABSTRACT

A LED illumination module has at least one LED (6). At a proximal side there is a first electric connection contact (8) and at an axially oppositely directed distal side there is a second electrical connection contact (10) as well as a radiation region emitting radiation. The LED (6), at the second electrical connection contact (10), is contacted via an electrically conductive sleeve (14) which, distanced to the proximal end, is electrically conductively connected to the second connection contact (10) of the LED (6).

20 Claims, 10 Drawing Sheets

(51) Int. Cl.
  *G02B 23/24* (2006.01)
  *A61B 1/12* (2006.01)
  *F21V 23/06* (2006.01)
  *H01R 24/38* (2011.01)
(52) U.S. Cl.
  CPC ............... *A61B 1/12* (2013.01); *F21V 23/06* (2013.01); *G02B 23/2461* (2013.01); *A61B 1/0607* (2013.01); *H01R 24/38* (2013.01); *H01R 2201/12* (2013.01)
(58) Field of Classification Search
  CPC ....... A61B 1/0676; A61B 1/12; A61B 1/0607; H01L 33/641; G02B 23/2461
  See application file for complete search history.

(56) References Cited

U.S. PATENT DOCUMENTS

| | | | |
|---|---|---|---|
| 2003/0006423 A1* | 1/2003 | Loh | H01L 25/0753 257/99 |
| 2003/0025450 A1* | 2/2003 | Katayama | G09F 9/33 313/512 |
| 2003/0035048 A1* | 2/2003 | Shipp | H04N 7/183 348/68 |
| 2003/0116838 A1 | 6/2003 | Wu | |
| 2004/0227146 A1 | 11/2004 | Wu | |
| 2005/0280019 A1* | 12/2005 | Konno | H01L 33/486 257/100 |
| 2006/0183977 A1* | 8/2006 | Ishigami | A61B 1/00177 600/179 |
| 2007/0080362 A1* | 4/2007 | Scotch | H01L 33/641 257/99 |
| 2008/0045802 A1* | 2/2008 | Brandstaetter | A61B 1/0607 600/199 |
| 2008/0128740 A1* | 6/2008 | Yamashita | A61B 1/0676 257/99 |
| 2009/0306478 A1* | 12/2009 | Mizuyoshi | A61B 1/0638 600/178 |
| 2010/0314986 A1* | 12/2010 | Gershaw | F21K 9/69 313/46 |
| 2011/0092772 A1 | 4/2011 | Weber et al. | |
| 2012/0211793 A1* | 8/2012 | Bergmann | H01L 24/29 257/99 |
| 2013/0114241 A1* | 5/2013 | van de Ven | H05B 33/0863 362/84 |

* cited by examiner

LED ILLUMINATION MODULE

CROSS REFERENCE TO RELATED APPLICATIONS

This application is a United States National Phase Application of International Application PCT/EP2014/050130 filed Jan. 7, 2014 and claims the benefit of priority under 35 U.S.C. § 119 of German Patent Application 10 2013 201 808.8 filed Feb. 5, 2013 the entire contents of which are incorporated herein by reference.

FIELD OF THE INVENTION

The invention relates to an LED illumination module with at least one LED which at a proximal side comprises a first electrical connection contact and at an axially oppositely directed distal side comprises a second electrical connection contact as well as a radiation region emitting radiation, as well as to an endoscopic apparatus with at least one such illumination module.

BACKGROUND OF THE INVENTION

Light diodes (LED) are known for illumination purposes in medical instruments or apparatus, in particular in endoscopes. Thereby, such LEDs can be placed at the distal end of the endoscope, so that one can make do without fibre optics in the instrument, and the illumination module can be placed directly where the illumination is needed. This lends itself with rigid as well as with flexible endoscopes. The problem with the use of LEDs is the occurring significant waste heat which must be led away from the LED, in order not to compromise its functioning. Moreover, a risk to the adjacent tissue due to too great heating can moreover be given, so that the heat dissipation must preferably be effected such that an undesired heating of the adjacent tissue is avoided. Moreover, a secure contacting and fixing of an LED in an endoscope is necessary.

SUMMARY OF THE INVENTION

With regard to this problem, it is an object of the invention to provide an LED illumination module as well as a medical apparatus with at least one such LED illumination module, in which apparatus an LED can be electrically contacted in a simple manner and a good heat dissipation can be simultaneously ensured.

The LED illumination module according to the invention is preferably designed for application in a medical and in particular in an endoscopic apparatus or endoscope.

The LED illumination module comprises at least one LED, which on a proximal side comprises a first electrical connection contact and on a distal side which is directed axially opposite comprises a second electrical connection contact. The LED or the LED chip thus has a vertical construction with only one electrical contact surface on the chip lower side, specifically the first proximally directed connection contact. The second, axially oppositely directed connection contact at the distal side is thus situated on the upper side of the LED or the LED chip, which is the side of the LED which emits the radiation. I.e. the axially directed distal side of the LED, on which the second electrical connection contact is situated, comprises a radiation-emitting region. Radiation is thereby to be understood as the light of the spectral region visible to the human eye, as well as the radiation of the short-wave and long-wave spectral regions which are adjacent to this and are not visible to the human eye. Such radiation can be applied in medical instruments, for example for therapeutic purposes, for example for photodynamic therapy or for example for auto-fluorescence diagnosis.

According to the invention, an electrically conductive sleeve is provided for electrically contacting the LED. The sleeve is preferably designed in a circularly cylindrical manner. The sleeve is electrically conductively connected to the second connection contact of the LED, in a manner distanced to the proximal end of this sleeve. The electrically conductive sleeve thus forms an electrical connection from the distal side of the LED and the second connection contact which is situated there, to the proximal side, so that the distal-side connection and the proximal-side connection of the LED then via the sleeve can be contacted there via a connection lead. A simple contacting of the LED is possible in this manner. Larger contact surfaces for the electrical contacting are in particular created. Moreover, this construction permits a good heat dissipation or removal. The use of a LED with a vertical construction, i.e. with electrical contacts on the upper side and lower side, has the advantage that the lower side of the LED can be contacted in a direct and large-surfaced manner by an electrical connection lead without the intermediate connection of a further circuit board, so that an improved heat dissipation via the connection lead is possible in the proximal direction. The surrounding sleeve can likewise serve for heat dissipation.

The sleeve preferably surrounds the LED, and/or an electrical conductor (lead) or in particular a sheath insulating this, which leads to the first electrical connection contact. It is ensured by way of this design that the first electrical conductor can provide a large contact surface for the first electrical connection contact at the proximal side of the LED, and the sleeve can be arranged in the peripheral region in a relatively thin and space-saving manner, in order to contact the second electrical connection contact at the distal side of the LED via the sleeve. For this, the sleeve can extend past the LED in a fully peripheral or only in a peripheral part region, up to the distal side of this, in order to contact the second electrical connection contact. It is also possible, departing from the distal end of the sleeve, for a web or a tab to extend in the axial direction past the LED to its second electrical connection contact.

The sleeve can surround the LED and/or the first electrical conductor or in particular a sheath insulating this, in a fully peripheral or part-peripheral manner. The sleeve forms a closed ring if it surrounds the LED and/or the first electrical conductor over the whole periphery. If it surrounds the LED and/or the first electrical conductor in a partially peripheral manner, then the sleeve preferably extends over a periphery of greater than 180° and further preferably over a peripheral region of greater than 270°, around the LED and/or the first electrical lead. Thus the sleeve can comprise a slot in the axial direction. The sleeve can be given a spring effect in this manner, and this effect permits the sleeve for example to be held in a clamped manner, on an insulating sheath surrounding the LED or the first electrical lead. For this, the sleeve can be designed such that in its relaxed condition, it has an inner diameter which is smaller than the outer diameter of the components to be received in the inside of the sleeve, for example the outer diameter of the insulating sheath. The sleeve is elastically deformed and widened when placing on the sleeve, so that it can be held on the outer periphery of the inner-lying components in a clamped manner by way of the elastic restoring forces.

Further preferably, the sleeve is electrically conductively connected to the second connection contact of the LED, in the region of the distal end of this sleeve. This electrically conductive connection can be situated directly at the distal end of the sleeve, but also distanced to the distal end by a certain amount. In the region of the distal end it then means that the electrical contacting seen in the axial direction is situated closer to the distal end than to the proximal end.

The sleeve preferably comprises a radially inwardly directed tab or a radially inwardly directed projection, which are electrically conductively connected to the second connection contact of the LED. The tab is preferably designed as one piece with the sleeve. The radially inwardly directed tab or the radially inwardly directed projection can be directly formed on the distal end of the sleeve, but also arranged distanced to the distal end of the sleeve. The radially inwardly directed tab or the radially inwardly directed projection can be distanced to the distal end of the sleeve in the proximal direction. Thereby, the tab or the projection is preferably situated closer to the distal end of the sleeve than to the proximal end of the sleeve. Alternatively, the radially inwardly directed tab or the radially inwardly directed projection can also be distanced to the distal end of the sleeve in the distal direction. Thus a web or a tab can firstly extend in the distal direction away from the distal end of the sleeve, wherein the projection or the radially inwardly directed tab then extends radially inwards from this axially directed web. For this, the tab can be designed in a bent manner. The sleeve can thus be pushed over the LED from the distal side, until the tab comes to bear on the contact on the distal face side of the LED. There, it can be contacted in a known, suitable manner, for example by way of soldering or another suitable electrically conductive connection technique.

The first electrical connection contact of the LED, i.e. the electrical connection contact situated at the proximal side is connected directly to a first electrical conductor for the electrical connection of the LED. This, as explained above, has the advantage that the heat transfer from the LED into this electric conductor is improved and that no heat-insulating components such as a circuit board, need to be arranged between the connection contact and the lead. The conductor is preferably contacted by the lower side of the LED in a direct and large-surfaced manner. A contact of the whole proximal surface of the LED on the electrical conductor is particularly preferably achieved.

The sleeve at its proximal end or in its peripheral region can be connected directly or indirectly to a second electric conductor for the electric connection of the LED. Such a conductor for example can be soldered directly to the sleeve or be in electric contact with this in another suitable manner.

Further preferably, the sleeve in the axial direction preferably has a greater length than the LED. It is thus ensured that the sleeve as an electric conductor acts at least up to the proximal side of the LED, and preferably completely encompasses or encloses the LED at the peripheral side.

The sleeve however can also be designed slotted in the longitudinal direction, as described above.

The sleeve can therefore also serve for the removal or dissipation of the heat exiting from the LED. Moreover, the sleeve can serve for guiding and protecting the LED. The sleeve can therefore protect the sensitive inner-lying parts, such as e.g. the LED and its contacting, during storage and assembly. The sleeve can moreover serve as a guide aid in the lateral direction and as an abutment in the longitudinal direction on assembly. For this, the sleeve preferably has a sufficient length in comparison to its diameter. The sleeve can moreover function as an interface for the fixation of the LED illumination module in the inside of a medical apparatus, in particular an endoscope. The sleeve in the distal direction preferably does not project or essentially does not project beyond the distal side of the LED, so that the sleeve with the LED can be placed in the inside of the endoscope as close as possible to the exit window. The sleeve at the distal end preferably projects beyond the distal end of the LED only by the thickness of the tab which serves for contacting the second electric connection contact.

The first electric connection contact, i.e. the connection contact which is situated at the proximal side of the LED, is electrically conductively connected to a counter-contact surface of the first electric conductor for the electric connection of the LED, wherein the counter-contact surface has an equal or larger surface than the first connection contact. In this manner, a direct heat transfer via the complete connection contact surface into the connected electric conductor can be achieved, by which means the heat dissipation in the proximal direction via the electric conductor is improved. The connection contact can be soldered or bonded in an electrically conductive manner to the counter-contact surface for example.

Thus the first connection contact can have a rectangular, in particular square contact surface, and the counter-contact surface a round, in particular circular shape, wherein the diameter of the counter-contact surface further preferably corresponds to at least the length of a diagonal of the rectangular or square contact surface. It is thus ensured that the connection contact can bear on the counter-contact surface in a complete manner.

According to a further preferred embodiment, a coaxial cable is used for the electric connection of the LED, from which an inner conductor forms a first electric conductor connected to the first connection contact of the LED, and an outer conductor is connected to the sleeve in an electrically conductive manner. A very large cross-sectional area of the conductors can be made available with such a coaxial cable, and this large area permits good heat dissipation in the proximal direction. The inner conductor of the coaxial cable in particular can be designed with such a large cross section that it can serve for the heat dissipation from the LED in the proximal direction. The inner conductor preferably has a cross-sectional area which corresponds at least to the cross-sectional area of the first electric connection contact, so that the first electric connection contact can bear on the face side of the inner conductor of the coaxial cable over the complete surface. The sleeve provided according to the invention simplifies the contacting of such a coaxial cable, since the inner conductor of the coaxial cable can thus directly be connected to the proximal-side connection contact of the LED, whereas the sleeve permits a contacting of the outer conductor of the coaxial cable to the connection contact at the distal-side surface of the LED in a simple manner.

According to a further embodiment, the inner space or interior of the sleeve which surrounds the LED can be filled with a filling material which is transparent to the radiation emitted by the LED. The sleeve thereby forms a container or a vessel which receives the filling material. This is particularly advantageous if the filling material is filled in liquid form. This filling material on the one hand can serve for the fixation of the LED in the inside of the sleeve, and on the other hand can improve the removal of heat from the LED to the sleeve. The filling material can moreover also contribute to the stability and strength of the sleeve and of the LED illumination module as a whole. Thus the sleeve filled with the filling material has a greater strength with respect to external mechanical influences if a filling material having a suitable high strength after curing/hardening is used. Moreover, it can permit an optical influencing of the radiation at the exit side of the LED, at which the radiation exits, if it is designed transparently for the radiation emitted by the LED. For example, by way of a suitable selection of the refractive index it can permit a desired refraction of the radiation at the transition at the LED into the filling material, and as the case may be, from the filling material to an exit window or to further optical components. The filling material, for example a cast mass which is situated distally of the LED, can moreover contain a converter material, which for example shifts, widens or changes a wavelength region of the light emitted by the LED. In the case of a suitable selection of the filling material, the LED and the electrical connection contacts or at least one electric connection contact can moreover be protected from moisture by the filling material. Thereby, the filling material is preferably to be selected such that it can withstand the respective preparations methods for medical apparatus, e.g. autoclaving.

According to a further preferred embodiment, the sleeve is surrounded by a thermally insulating sheath at its outer periphery. A heat dissipation or outward radiation of heat from the sleeve to the outside is avoided by way of this, so that a heating of the regions surrounding the LED and the sleeve is reduced. The heat dissipation is preferably optimised such that the greatest part of the heat is transmitted in the proximal direction from the LED onto the electric connection lead and/or from the sleeve onto the proximally connecting components.

The thermally insulating sleeve for example can be formed of a plastic material which is deposited directly onto the sleeve or surrounds the sleeve.

The sleeve according to a further embodiment of the invention can be arranged and designed such that a distal end of the sleeve is distanced to the distal side of the LED in the proximal direction. I.e. the sleeve then in the distal direction does not extend up to the distal end of the LED. In this embodiment example, the contacting of the second electric connection contact of the LED can then be effected via a web or a tab, which extends in the axial direction from the distal end of the sleeve past the LED up to its distal side and thus contacts the second electric connection contact at the distal side of the LED. For this, a tab or projection can extend radially inwardly to the second electric connection contact, in a manner departing from this tab or web. The web extending away from the sleeve in the distal direction for example can be bent at its distal end for this.

According to an alternative embodiment of the invention, the sleeve can extend axially beyond the distal end of the LED, and a window can be arranged in the inside of the sleeve, at the distal end of this sleeve. The sleeve therefore forms a carrier for the window which is then situated distally of the LED. A free space which is present between the LED and the window as the case may be can be filled with a suitable transparent filling material as described above. This filling material, as described above, can have targeted optical characteristics or properties or for example also contain a converter material. The window which in particular is manufactured of an amorphous material, e.g. of glass or a crystalline material, e.g. sapphire, has an outer periphery which corresponds to the inner periphery or inner diameter of the sleeve and thus can preferably bear on the inner periphery of the sleeve in a sealed manner. The window can be bonded or soldered to the sleeve or preferably sealingly connected to it in another manner. The window thus forms an axial-side sealing of the LED illumination module. A sealed encapsulation of the electric components such as the LED and the electric connection contact can thus be achieved in the LED illumination module itself. This on the one hand provides a protection for these components before the final assembly in a medical instrument or apparatus, but on the other hand protects the components in the medical instrument from penetrating moisture at a later stage. The window moreover contributes to the stability of the LED illumination module and of the sleeve, in particular with regard to lateral effects of force. The LED module is thus protected from damage to an increased extent, before and during the assembly. The window lies in the sleeve preferably distally of a projection which extends radially inwards from the sleeve or of a tab which extends radially inwards and is for contacting the distal-side connection contact of the LED.

In a further preferred embodiment, the sleeve can be surrounded by a further outer sleeve which extends axially beyond the distal end of the previously described sleeve and in whose inside a window is arranged at the distal end. This outer sleeve can likewise be designed in an electrically conductive or also electrically insulating manner. The window has an outer diameter or an outer periphery which corresponds to the inner diameter or the inner periphery of the outer sleeve, so that the window with its outer periphery bears with its outer periphery on the inner periphery of the outer sleeve, preferably in a sealed manner. The window which is preferably formed from glass or a crystalline medium, can be bonded or soldered to the outer sleeve or connected to it in another, preferably sealed which is to say tight manner. The outer sleeve with the window can be pushed over the electrically conductive sleeve surrounding the LED, from the distal end. The outer sleeve is then preferably connected, for example soldered or bonded to the inner-lying sleeve in a sealed manner. This design has the advantage that the sleeve can be soldered to the distal-side connection contact of the LED for contacting the LED, and the sleeve as the case may be can be filled with a filling material at the distal side of the LED, before placing on the outer sleeve. This can then be accomplished from the open distal side of the sleeve. The sleeve is subsequently sealingly closed by way of pushing over the outer sleeve with the window. Thereby the outer sleeve preferably has such an axial length, that recesses or operating in the inner sleeve are enclosed by the outer sleeve at the outer periphery. Such openings or recesses can be formed for example by way of a radially inwardly bent tab of the inner sleeve for contacting the distal-side connection contact of the LED. With this embodiment too, a completely sealed and encapsulated LED illumination module is preferably created, and this is projected from damage and moisture before and during assembly. The window and the outer sleeve contribute to the further stabilization of the LED illumination module.

The windows described above, which can be arranged in the sleeve or outer sleeve, on installation of the LED illumination module into a medical apparatus or endoscope can preferably form the distal-side, outer window of the illumination module. I.e. no further window needs to be provided in the endoscope at the distal side. The sleeve or, as the case may be, the outer sleeve, are then connected, for example bonded, to a surrounding wall of the instrument or of the endoscope, preferably in a sealed manner.

The LED illumination module of the invention, as has been described above is particularly preferably designed for application in a medical apparatus and in particular in an endoscope. The LED illumination module according to the invention, in such apparatus, in particular is suitable for arrangement at the distal end of the apparatus. With regard to an endoscope, this is that end which is introduced into the body. A heating is often to be avoided in this region, in order to prevent damage to the surrounding tissue. Inasmuch as this is concerned, with these apparatus, it is desirable to be able to lead the heat out of the examination region in the proximal direction in a targeted manner. The direct contacting of the LED with an electric connection lead and the described application of the sleeve for contacting thereby permit an optimized heat dissipation in the proximal direction via the connection lead. This however is not only advantageous with medical endoscopes, but also with technical endoscopes, so that the use is not limited to medical endoscopes.

The subject matter of the invention is moreover a medical apparatus with at least one LED illumination module according to the previous claims. Such a medical apparatus is further preferably an endoscope. Thereby, it can be the case of a flexible or rigid endoscope.

According to a preferred embodiment of the medical apparatus, the sleeve of the LED illumination module with its distal face side bears on at least one abutment surface in the inside of a head of the endoscope. Thus the sleeve in the axial direction is fixed with the LED arranged in the inside, in the inside of the endoscope. The abutment or contact surface can thereby be formed by a viewing window or exit window at the distal end of the head of the endoscope.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
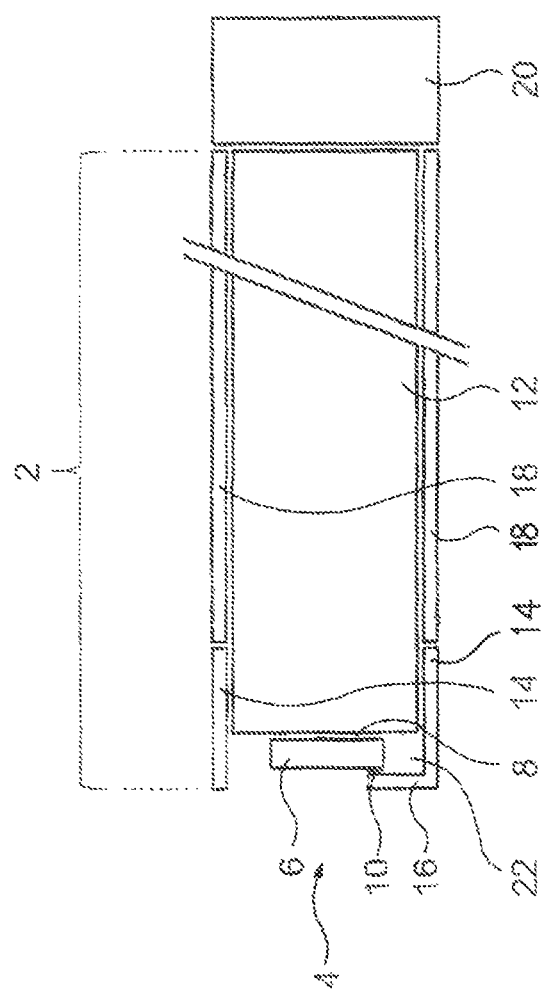
FIG. 1 is a schematic sectioned view showing the construction of a LED illumination module according to the invention.

The basic construction of a LED illumination module according to the invention is firstly described by way of the schematic sectioned view in FIG. 1. The LED illumination module at its distal end comprises a LED or an LED chip 6 which emits radiation or light in the distal direction. The LED chip 6 has a vertical construction, i.e. it has a first electrical connection contact 8 at its proximal side, and a second electrical connection contact 10 at its distal side which also form the exit side for the radiation or for the light emitted by the LED chip 6. The first connection contact 8 is connected to a first electric conductor 12. One can recognize that a large-surfaced contacting between the first connection contact 8 and the first electric conductor 12 is possible. The LED chip 6 bears with its first connection contact 8 on the face side of the first electrical conductor 12 over the whole surface, so that a good heat transfer in the proximal direction is achieved here. The second electric connection contact 10 of the LED chip 6 is contacted by a sleeve 14. The sleeve 14 is electrically conductive, for example is designed from metal and peripherally surrounds the LED chip 6. The sleeve 14 at the distal end of this comprises a radially inwardly directed tab 16 which contacts the second electric connection contact 10 at the distal side of the LED chip 6.

The sleeve 14 at the proximal end is connected to a second electric conductor 18. The second electric conductor 18 forms the return lead, whereas the first electrical conductor 12 forms the forward lead. Both are electrically insulated from one another in a manner which is not represented in detail here. A coaxial arrangement is shown here. Preferably, the first electric conductor 12 and the second electric conductor 18 as well as the associated electrical insulations are designed in a flexible manner, so that the illumination unit 2 can be applied in a flexible endoscope. The first electric conductor 12 and the second electric conductor 18 at their proximal end are connected to an energy source 20 which here is represented in a schematic manner.

The free space 22 surrounding the LED chip 6 can be filled with a suitable filling material. Inasmuch as this filling material also extends beyond the distal surface of the LED chip 6, this is preferably designed transparently for the radiation emitted by the LED 6 or the emitted light. The filling material can however also contain a converter material which absorbs at least a part of the radiation emitted by the LED 6 and converts it into radiation which is to be assigned to the longer-waved spectral region. Optical influences of the emitted radiation or of the emitted light, in particular at the transition into a distally connecting exit window can be achieved by way of the suitable selection of the refractive index. The radiation for example can be refracted in a suitable manner. The free space 22 for example can be filled with silicone, epoxy resin or a similar filling material which has the desired optical characteristics, moreover protects the LED chip and fixes it in the housing. The free space 22 can alternatively also be filled with air.

The connections of the LED chip 6 to the first electric conductor 12 and the sleeve 14 can be effected in the known manner, for example by way of soldering or conductive adhesive. The sleeve 14 is preferably designed in a thin-walled manner, in order to keep the lateral extension of the illumination module 2 low. The tab 16 has a size which is sufficient to contact the connection contact 10, but is preferably formed in such a small and slim manner that ideally it does not at all restrict the light emission or radiation emission of the LED chip 6 or at least as little as possible. The sleeve 14 projects beyond the LED chip 6 in the distal direction and in particular also in the proximal direction, so that the LED chip 6 is arranged protected in the inside of the sleeve. The sleeve 14 can also serve for the fixation and positioning of the LED chip 6 in a medical instrument, for example in an endoscope. The overhang in the distal direction however is selected so small, that the tab 16 can only just extend beyond the distal side of the LED chip 6. The distance of the LED chip to a distally connecting window or further optical components can be kept as low as possible by way of this.

Figure 2:
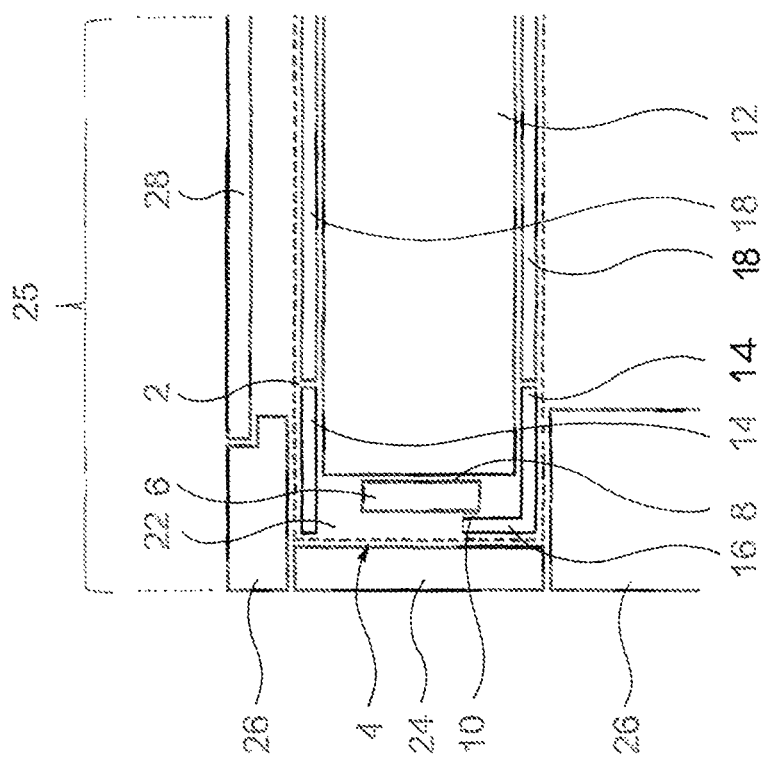
FIG. 2 is a schematic sectioned view showing the arrangement of a LED illumination module according to FIG. 1, in a flexible endoscope.

FIG. 2 shows the possible installation of the LED illumination module 2 into a medical apparatus, here for example a flexible endoscope. The LED illumination module 2 which is shown in FIG. 1, in FIG. 2 with its distal end 4 bears on a window 24 which forms the exit window at the distal end of the endoscope. The window 24 for example is designed as a glass platelet or transparent plastic platelet. The window 24 is embedded into the face-side wall 26 of an endoscope head or endoscope headlet (small head). The endoscope headlet is arranged at the distal end of an endoscope flexible tube or endoscope shank 28, in whose interior the LED illumination module 2 is received. It can be recognized that the sleeve 14 is suitable for fixing the LED chip 6 previously embedded in the sleeve 14, in the face-side wall 26 of the endoscope headlet in a suitable recess and for positioning it directly behind the window 24.

Figure 3:
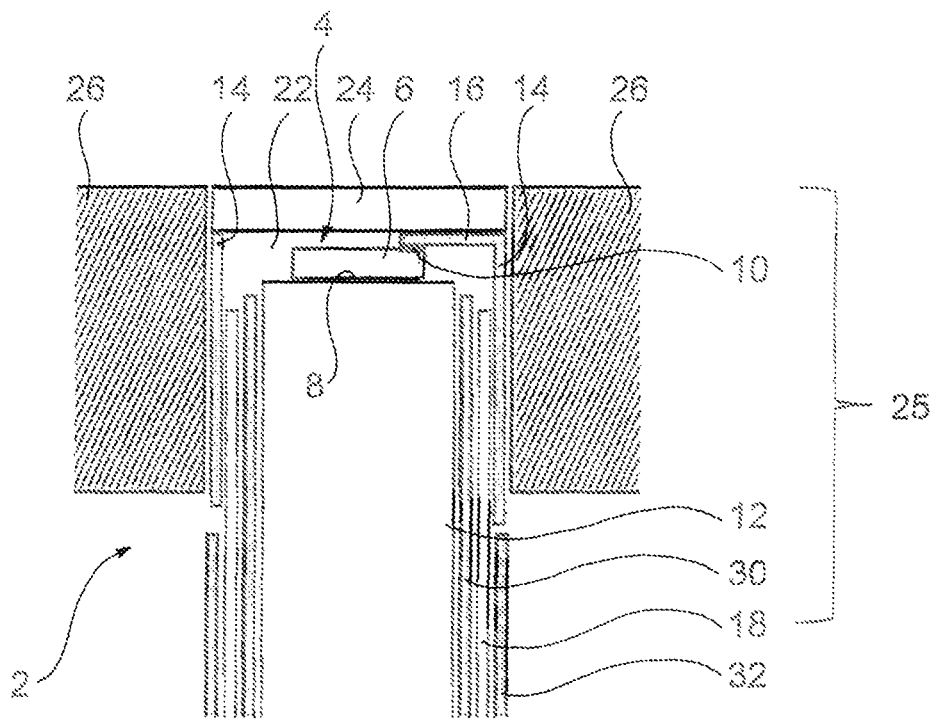
FIG. 3 is a schematic sectioned view of the arrangement of a LED illumination module according to the invention, in an endoscope.

FIG. 3 shows a more specific design of the arrangement according to FIG. 2, with which the required insulations in the electric connection lead are additionally shown. The first electrical conductor 12 forms the core of a coaxial cable and is peripherally surrounded by a first electrical insulation 30. The first electrical insulation 30 in turn is peripherally surrounded by the second electric conductor 18 which forms the shielding of the coaxial cable. The second electric conductor for its part is peripherally surrounded by a second electrical insulation 32. What can be recognised is that the first electric conductor 12 has a significantly larger cross section than the second electric conductor 18. Thus the first electric conductor 12 can bear on the proximal side of the LED chip 6 over the whole surface or almost over the whole surface and dissipate the greater part of the occurring waste heat in the proximal direction through the coaxial cable. The larger cross section forms a low thermal resistance. The first and the second insulation 30 and 32 as well as the second electrical conductor 18 are however preferably designed as thinly as possible in the radial or lateral direction, in order to keep low the lateral extension of the illumination unit 2. Moreover, a low thermal resistance of the coaxial cable in the lateral direction is accomplished, so that the heat can be released from the cable into the peripheral region. Thus the heat which is led away proximally from the LED chip 6 can then exit in the radial or lateral direction out of the proximally connecting connection cable. The distal end of the instrument however is thus thermally loaded or heated to a lesser extent. The second electrical conductor 18 is led into the inside of the sleeve 14 and there is contacted with the sleeve at the inner side. The sleeve 14, as described previously, then creates the electrical contact to the connection contact 10 at the distal side of the LED chip 6.

Figure 4:
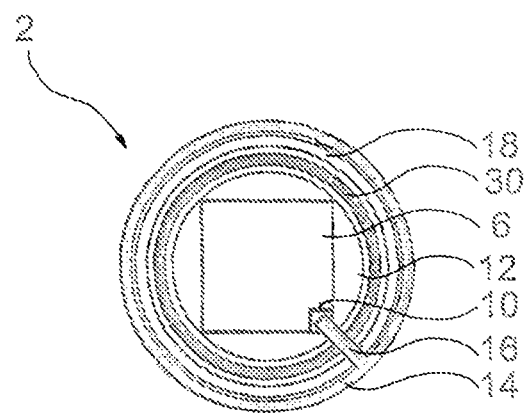
FIG. 4 is a plan view of the LED illumination module according to FIG. 3, from the distal direction.

FIG. 4 shows a plan view of the LED module 2 in the inside of the endoscope head which is shown in FIG. 3. It can be recognised that the sleeve 14 peripherally surrounds the LED chip 6 and that only the narrow tab 16 distally covers the LED chip 6 at a corner, in order to contact the connection contact 10. One can moreover recognise that the square LED chip 6 lies completely on the round distal face side of the first electric conductor 12, i.e. the core of the coaxial cable. For this, the first electrical conductor 12 has a diameter which corresponds essentially to the diagonal of the LED chip 6.

Figure 16:
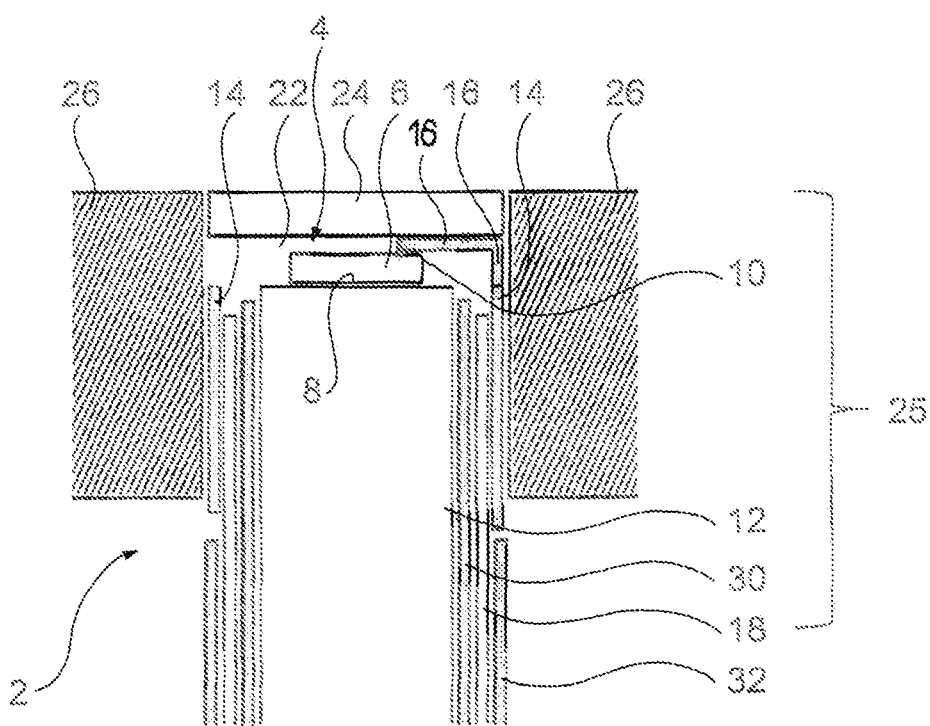
FIG. 16 is a sectional view of a further possible arrangement of a LED illumination module in an endoscope.

A modification of the embodiment according to FIG. 3 is shown in FIG. 16. The embodiment shown in FIG. 16 differs from the design according to FIG. 3 in that the sleeve 14 does not extend peripherally of the LED 6 up to the window 24 in a fully peripheral manner. In contrast, in this embodiment example, the sleeve 14 in the longitudinal direction ends essentially with the first electrical conductor 12. Only the tab 16 extends firstly in the axial extension of the sleeve 14 and then angled radially inwards beyond the distal face end of the sleeve 14. Thus, the tab 16 extends in a web-like manner past a peripheral side of the LED 6 up to its distal face side, where the radially inwardly angled part of the tab 16 then contacts the second connection contact 10. The design according to FIG. 16 otherwise corresponds to the design according to FIG. 3, so that with regard to further features, the previous description is referred to.

Figure 5:
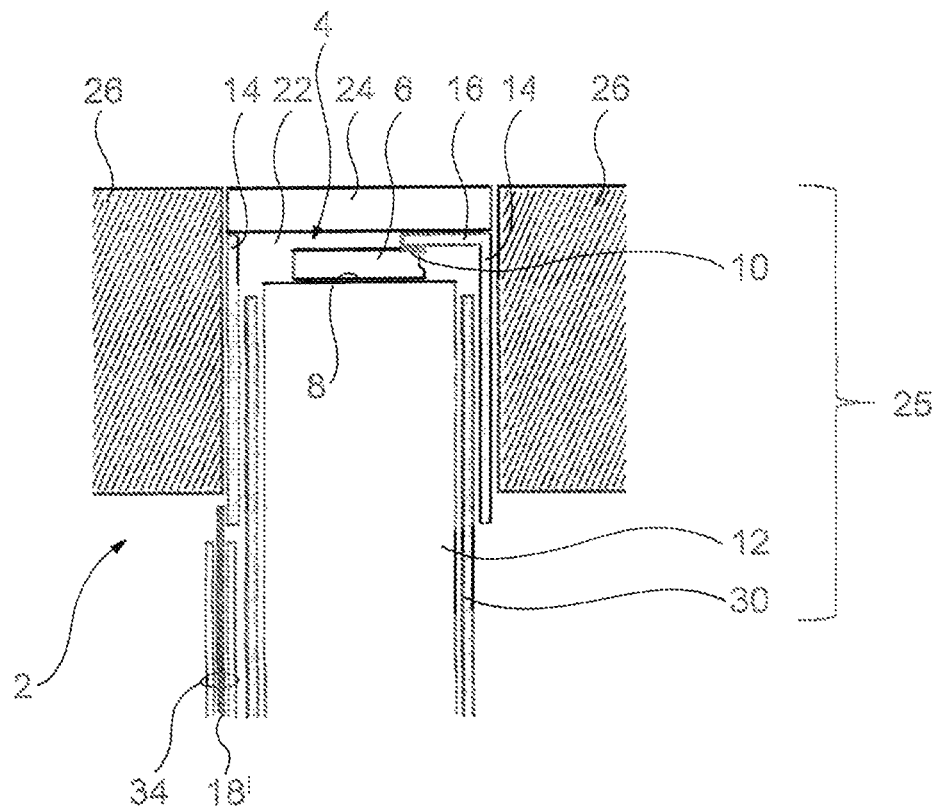
FIG. 5 is a schematic sectional view showing a further possible arrangement of a LED illumination module according to the invention in an endoscope.
Figure 6:
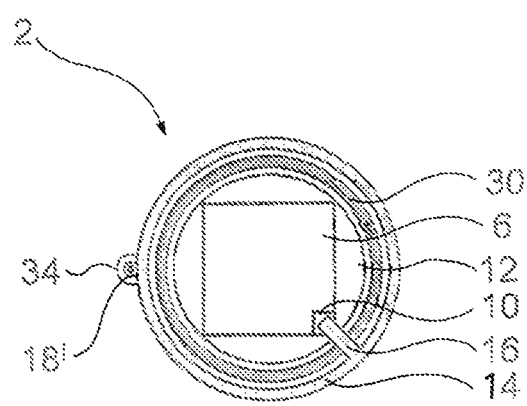
FIG. 6 is a plan view of the illumination module according to FIG. 5.

FIG. 5 shows an alternative construction of an endoscope headlet 25, in particular of a flexible endoscope. Here too, the LED illumination module 2 is arranged in a recess of the face-side wall 26 in a manner directly adjacent a window 24. The sleeve 14 thereby with its distal end and in particular with the tab 16 directly abuts the proximal side of the window 24, as is shown with the embodiments according to FIGS. 2 and 3. With the embodiment according to FIG. 5, the LED chip 6 at its proximal side, i.e. at its first electrical connection contact 8 is also in contact with the face side of a first electrical conductor 12. Thereby, the first electrical conductor 12 again has a diameter which is so large, that it covers the complete or almost complete proximal side of the LED chip 6 and here ensures a good heat transfer with a low thermal resistance. The electrical conductor 12 is surrounded by the first insulation 30 and with this embodiment can be designed as a simple strand lead/cable. The second electrical conductor 18' is arranged in a separate electrical cable 34 and at the peripheral side is connected to the proximal end of the sleeve 14. The connection can likewise be effected by way of soldering, clamping, crimping, bonding with conductive adhesives or likewise. The arrangement according to FIGS. 5 and 6 compared to the arrangement according to FIGS. 3 and 4 has the advantage that the diameter or the lateral extension of the electrical connection lead can be reduced due to making do without the second insulation 32 and the second electrical conductor 18 in the peripheral region of the first electrical conductor 12, i.e. making do without the coaxial construction. The electrical conductor 12 can therefore be designed with a larger cross section or diameter, by which means the thermal resistance can be further reduced and the heat dissipation in the proximal direction improved. This embodiment is particularly suitable for endoscopes having a small available construction space, due to the small lateral extension/dimension.

Figure 7:
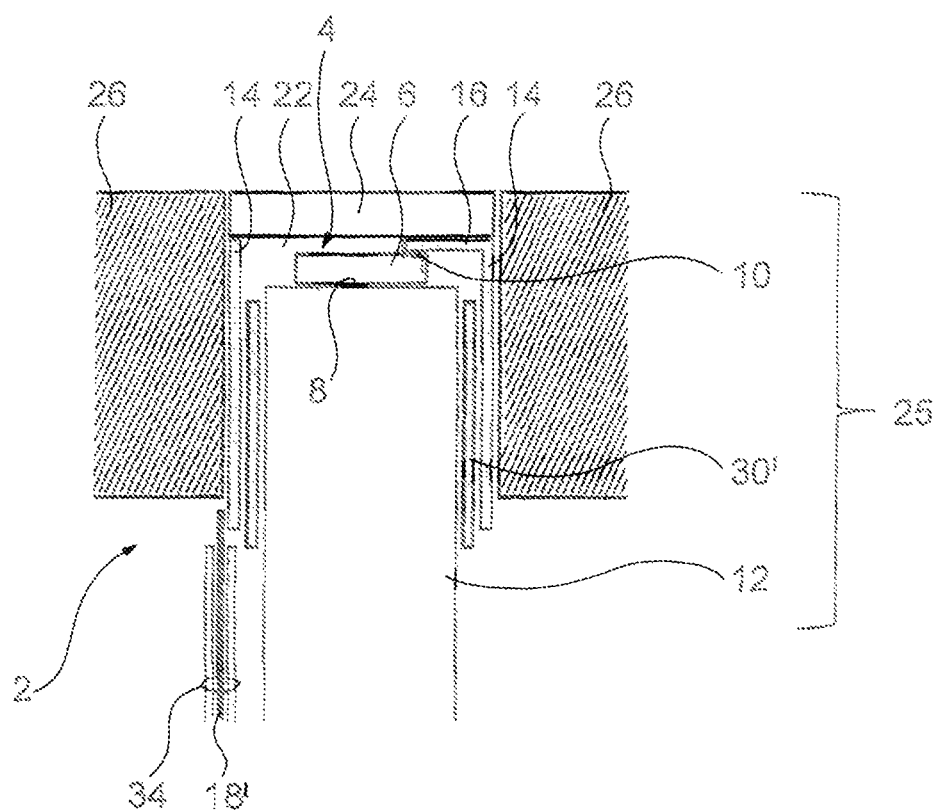
FIG. 7 is a schematic sectional view showing a further possible arrangement of an LED illumination module in an endoscope.

This design is yet further optimised by the embodiment represented in FIG. 7, with which one makes do without an insulation surrounding the forward conductor or the first electrical conductor 12 over the whole length. There, a first electrical insulation 30' peripherally of the first electrical conductor 12 is only provided within the sleeve 14, in order to avoid a short circuit between the sleeve 14 and the first electrical conductor 12. However, one has made do without a peripheral insulation of the first electric conductor 12 at the other side of the proximal end of the sleeve. A short circuit with the return conductor 18' here is only prevented by the insulation of the cable 34 containing the return conductor 18'. This has the advantage that waste heat can be radiated or led away in the radial direction in an improved manner, from the first electrical conductor 12, in the region which is free of a peripheral insulation.

Figure 8:
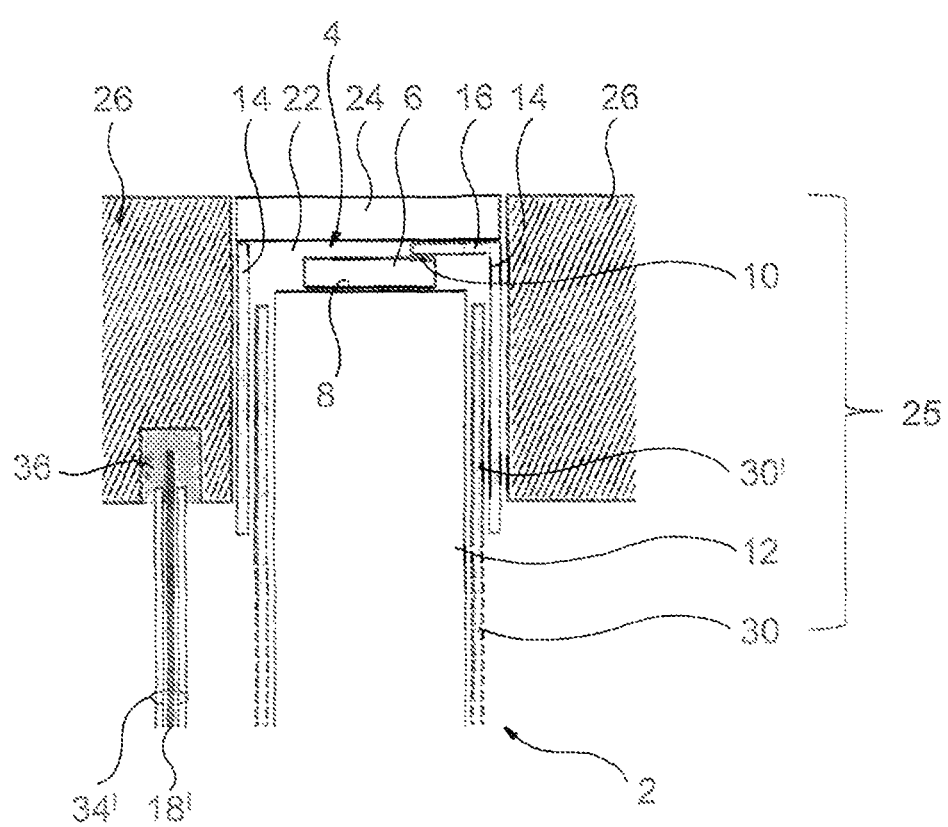
FIG. 8 is a schematic sectioned view showing a further possible arrangement of a LED illumination module in an endoscope.

FIG. 8 shows a further embodiment which represents a variant of the embodiments shown in FIGS. 5-7. The design of the first electrical conductor 12 thereby corresponds to the designs according to FIGS. 5-7, wherein selectively the first insulation 30, 30' can be extended beyond the proximal end of the sleeve 14, as is shown in FIG. 5, or however can end behind the proximal end of the sleeve 14, as is shown in FIG. 7. This is shown by the dashed course of the first insulation 30 in FIG. 8. In contrast to the embodiments according to FIGS. 5-7, with regard to the embodiment according to FIG. 8, the cable 34' is not connected directly to the sleeve 14, but to the face-side wall 26 of the endoscope headlet 25. For this, the second electrical conductor 18' in the inside of a pocket hole 36 in the face-side wall 26 can be soldered to this or electrically connected to it in another suitable manner. The wall 26 is designed in an electrically conductive manner and is in electrical contact with the outer periphery of the sleeve 14.

Figure 9:
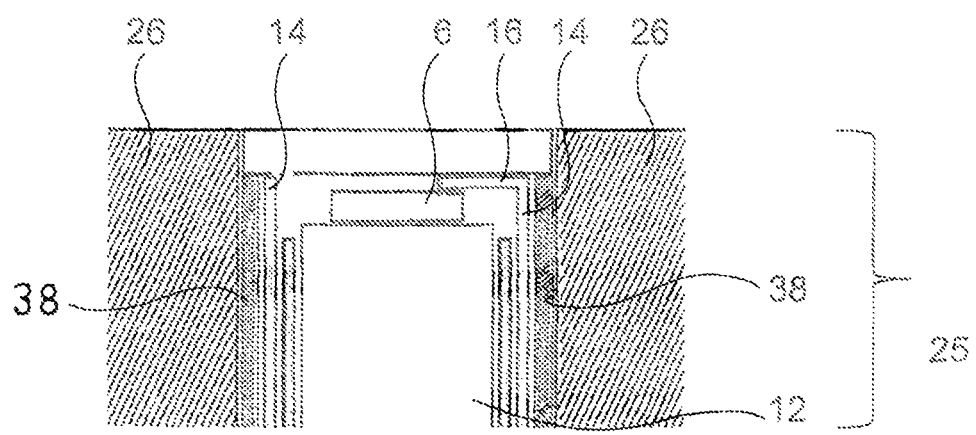
FIG. 9 is a schematic sectioned view showing a further possible arrangement of a LED illumination module in an endoscope.

FIG. 9 shows a further basic embodiment which could also be applied in combination with the previously described embodiments. With this embodiment, a sleeve 38 of a thermally insulating material is arranged between the wall 26 of the endoscope headlet 25 and the sleeve 14. This sleeve 38 increases the thermal resistance in the radial direction, in order to minimise a heating of the endoscope headlet 25 and in particular of the wall 26. It is thus ensured that the greater part of the waste heat is led away in the proximal direction via the first led 12. An electrical connection between the wall 26 and the sleeve 14 would have to be ensured through the sleeve 38 in combination with the embodiment according to FIG. 8. This on the one hand could be achieved by electrically conductive characteristics of the sleeve 38 or electrical leads which extend through the sleeve 38. Recesses could also be formed in the sleeve 38, and these permit an electrical contact through the sleeve.

Figure 10:
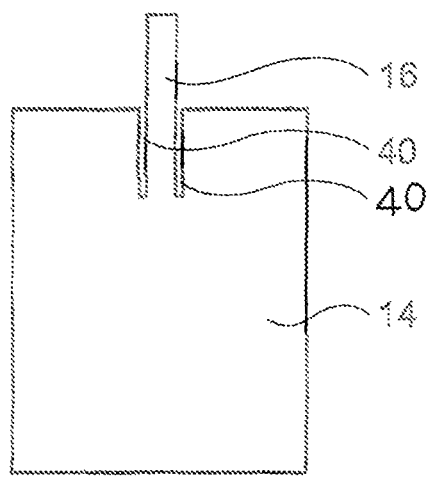
FIG. 10 is a view showing one of possible embodiments of a sleeve for a LED illumination module according to the invention.
Figure 11:
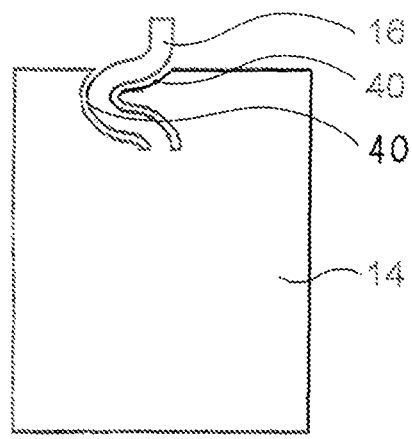
FIG. 11 is a view showing another of possible embodiments of a sleeve for a LED illumination module according to the invention.
Figure 12:
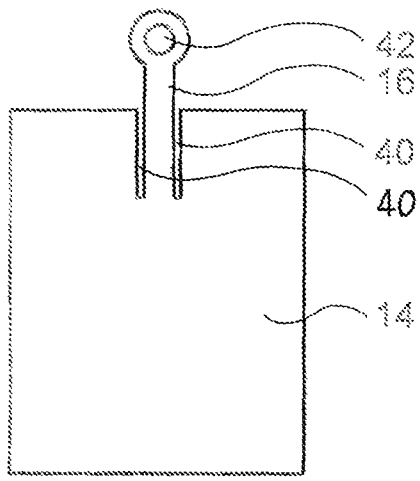
FIG. 12 is a view showing another of possible embodiments of a sleeve for a LED illumination module according to the invention.

FIGS. 10-12 show possible designs of the sleeve 14, wherein there, the tab 16 is not yet bent over in the direction transverse to the sleeve and still extends in the longitudinal direction of the peripheral wall of the sleeve. The three embodiments according to FIGS. 10-12 differ with regard to the design of the tab 16.

A movability of the tab 16 is desired, in order to ensure a certain movement ability or elasticity between the LED chip 6 and the sleeve 14. This is ensured by way of slot-like incisions or cuts 40 from the distal end into the sleeve 14, which delimit the tab 16. Thus the tab 16 is extended into the sleeve 14 and obtains an increased movablity, in order to avoid mechanical stresses. An even greater movability is achieved, in particular a spring effect is achieved in the axial direction, on account of the arcuate or meandering course of the incisions 40 according to the embodiment in FIG. 11.

Moreover, it is shown in FIG. 12 that the free end of the tab 16 comprises a contact surface with an inner-lying hole 42. Such a design could also be applied with the embodiments according to FIGS. 10 and 11. The hole 42 serves as a reservoir for solder when soldering the tab 16 onto the connection contact 10 of the LED chip 6. Moreover, it is ensured that solder cannot run away to the side and does not cover the radiation-emitting region of the LED chip. Moreover, less energy needs to be applied for soldering, and a laser can be applied for example as a soldering tool, and the laser radiation can come into direct contact with the solder in the hole 42, i.e. the tab 16 does not cover the solder of the soldering location.

Figure 13:
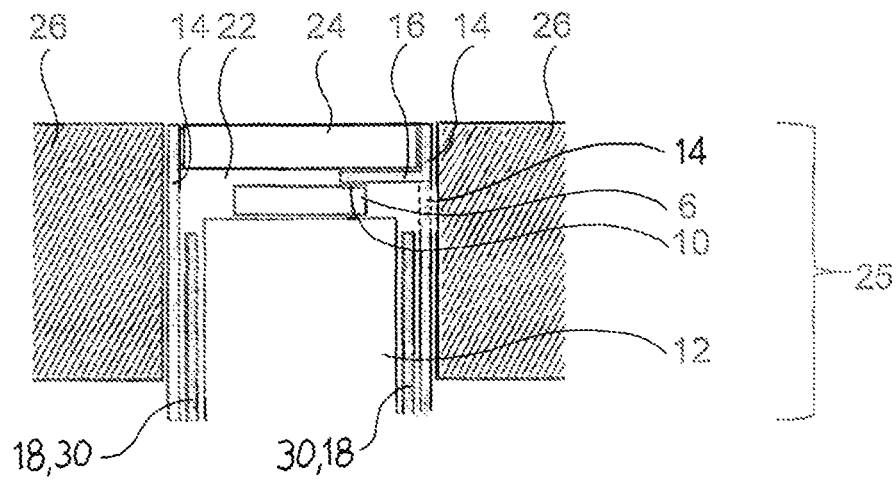
FIG. 13 is a schematic sectioned view showing one of further possible arrangements of a LED illumination module in an endoscope.

With the embodiment according to FIG. 13, the sleeve 14 is extended beyond the distal end of the LED 6, so that the sleeve 14 can receive a window 24. The window 24 is sealingly arranged on the inner periphery of the sleeve 14, for example bonded or soldered to this. The free space between the window 24 and the LED 6 or the first electrical conductor 12 is filled with a transparent filling material 22. Either a first insulation 30 or the second electric conductor 18 is arranged on the outer periphery of the first electric conductor 12, between the first electrical conductor 12 and the sleeve 14. The window 24 together with the filling material 22 and the sleeve 14 ensures that the LED module is sealingly closed to the outside, and in particular the LED 6 is arranged with the electric connection contacts in the inside in a protected manner. The sleeve 14 at the outer periphery is sealingly connected to the wall 26 of the medical instrument.

Figure 14:
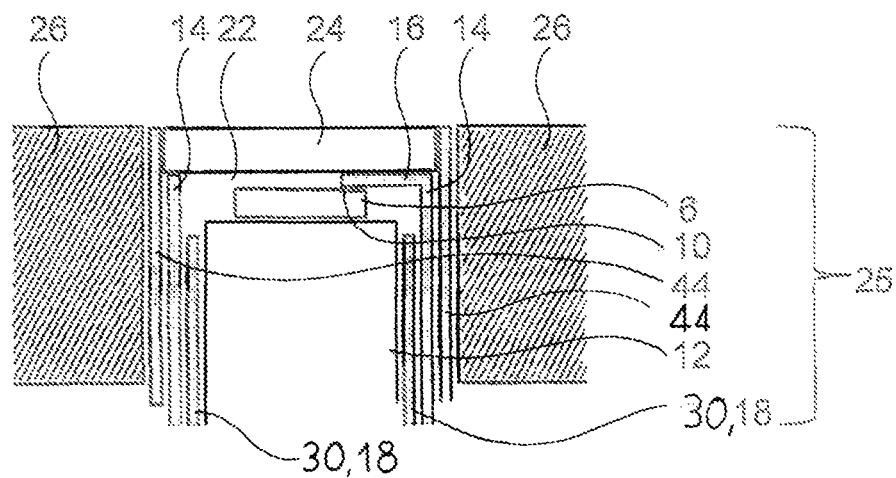
FIG. 14 is a schematic sectioned view showing another of further possible arrangements of a LED illumination module in an endoscope.

FIG. 14 shows a further variant, with which the window 24 is arranged in the inside of an outer sleeve 44. The window 24 sealingly bears on the inner periphery of the outer sleeve 44 at the distal end of this, and is peripherally sealing connected, for example soldered or bonded, to the outer sleeve 44. The outer sleeve 44 extends over a certain axial length at the outer periphery of the sleeve 14, preferably such that it extends to into the peripheral region of the first electrical conductor 12. Thus the outer sleeve 44 serves for the protection of the distal end of the LED illumination module and sealingly closes this. Compared to the embodiment shown in FIG. 13, this design has the advantage that the free space in the inside of the sleeve 14 surrounding the LED can firstly be filled with the filling material 22 from the distal end, and the sleeve 14 can then be closed from the distal end by way of pushing over the outer sleeve 44 with the window 24. The soldering of the tab 16 to the connection contact 10 at the distal side of the LED can thus also be effected through the open end of the sleeve 14, before the filling of the filling material 22. The outer sleeve 44 is sealingly connected to the sleeve 14, for example soldered or bonded. This design compared to the embodiment shown in FIG. 13 has the advantage that no openings in the LED module remain at the outer periphery. An opening remains in the region, in which the tab 16 is bent inwards out of the sleeve 14, with the embodiment according to FIG. 13.

Otherwise, the LED modules according to FIGS. 13 and 14 are designed as the previously described LED modules, so that their description is referred to.

Figure 15:
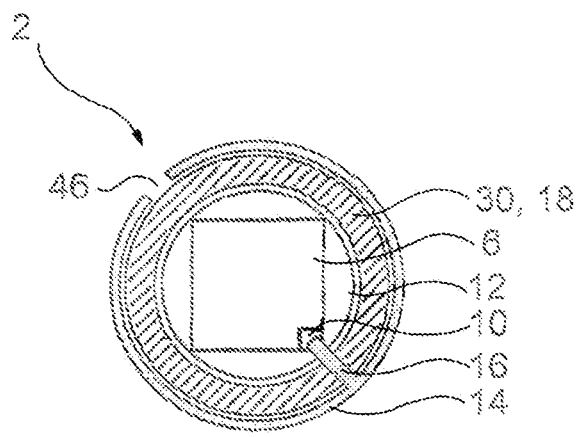
FIG. 15 is a plan view of a LED illumination module according to a further embodiment of the invention, shown from the distal direction.

FIG. 15 shows a sectioned view of an LED illumination module corresponding to the embodiment according to FIG.

4. It differs from the embodiment according to FIG. 4 in that the sleeve 14 is not designed in a fully peripheral manner but has an axially extending slot 46. This permits the design of the sleeve 14 such that it can be clamped onto the inner-lying components such as the insulation 30 and the second conductor 18, in a resilient manner. For this, the sleeve 14 is designed such that in its initial condition, it has a slightly smaller inner diameter than the outer diameter of the inner-lying components, so that the sleeve 14 elastically widens on applying onto the insulation 30 or the second electric conductor 18 and thus is clamped by way of a spring effect. The description of the embodiment according to FIG. 4 is otherwise referred to.

While specific embodiments of the invention have been shown and described in detail to illustrate the application of the principles of the invention, it will be understood that the invention may be embodied otherwise without departing from such principles.

The invention claimed is:

1. A medical apparatus comprising at least one LED illumination module comprising:
at least one light emitting diode (LED) having a proximal side comprising a first electrical connection contact and the at least one light emitting diode comprising a second electrical connection contact and a radiation region emitting radiation at a distal side of the LED, the distal side being axially opposite the proximal side;
an electrical conductor, at least the electrical conductor and the first electrical connection contact defining a first electrically conductive path; and
an electrically conductive sleeve extending to the second electrical connection contact at the distal side from a location beyond the proximal side, wherein the sleeve extends beyond the proximal side and at least a portion of the sleeve surrounds the LED, the electrically conductive sleeve being in direct contact with the second electrical connection contact on the distal side of the LED, at least the second electrical connection contact and the sleeve defining a second electrically conductive path, wherein the electrically conductive sleeve electrically contacts the at least one LED.

2. A medical apparatus according to claim 1, further comprising a medical apparatus structure, wherein the medical apparatus structure is an endoscope.

3. A medical apparatus according to claim 2, wherein the sleeve of the LED illumination module has a distal face side that bears on at least one abutment surface in an inside of a head of the endoscope.

4. A medical apparatus according to claim 1, wherein the sleeve surrounds the electrical conductor leading to the first electrical connection contact, and surrounds a sheath insulating the electrical conductor.

5. A medical apparatus according to claim 1, wherein the sleeve surrounds the electrical conductor and surrounds a sheath insulating the electrical conductor, in a fully peripheral or partially peripheral manner.

6. A medical apparatus according to claim 1, further comprising:
a power source, wherein the sleeve, in the region of its distal end, is electrically conductively connected to the second electrical connection contact of the LED and the sleeve is electrically conductively connected to the power source, wherein the second electrically conductive path extends from the power source to the distal side of the LED, at least a portion of the first electrically conductive path being located radially inward of the second electrically conductive path with respect to a longitudinal axis of the electrical conductor.

7. A medical apparatus according to claim 1, further comprising:
a power source, wherein the sleeve comprises a radially inwardly directed tab and an axial extent which are electrically conductively connected to the second electrical connection contact of the LED and the power source, the axial extent being integrally connected to the radially inwardly directed tab, at least a portion of the axial extent being located radially opposite the LED with respect to a longitudinal axis of the sleeve, the first electrically conductive path being connected to the power source, the first electrically conductive path being located at a spaced location from the second electrically conductive path.

8. A medical apparatus according to claim 1, wherein the first electrical connection contact of the LED is connected in a direct manner to the electrical conductor for electrical connection of the LED.

9. A medical apparatus according to claim 8, wherein the sleeve at a proximal end of the sleeve or in a peripheral region of the sleeve is connected to the electrical conductor for electrical connection of the LED.

10. A medical apparatus according to claim 8, wherein the electrical conductor comprises a counter-contact surface, the first electrical connection contact being electrically conductively connected to the counter-contact surface of the electric conductor for electrical connection of the LED, wherein the counter-contact surface has an equal or larger surface than the first connection contact.

11. A medical apparatus according to claim 10, wherein the first electrical connection contact has a rectangular or square contact surface and the counter-contact surface has a round shape, wherein a diameter of the counter-contact surface preferably corresponds at least to a length of a diagonal of the rectangular or square contact surface.

12. A medical apparatus according to claim 1, wherein the sleeve has a greater length in an axial direction than the LED, at least a portion of the sleeve extending to a position located axially beyond the LED with respect to a longitudinal axis of the sleeve.

13. A medical apparatus according to claim 1, further comprising a coaxial cable for an electrical connection of the LED, the coaxial cable having an inner conductor that forms the electrical conductor, connected to the first electrical connection contact of the LED, and an outer conductor that is electrically conductively connected to the sleeve.

14. A medical apparatus according to claim 1, wherein an inner space of the sleeve, which surrounds the LED is filled with a filling material which is transparent to a radiation emitted by the LED.

15. A medical apparatus according to claim 1, wherein a distal end of the sleeve is distanced to the distal side of the LED in the proximal direction.

16. A medical apparatus according to claim 1, wherein the sleeve extends axially beyond the distal side of the LED, and a window is arranged at the distal end of the sleeve in the inside of the sleeve.

17. A medical apparatus according to claim 1, further comprising an outer sleeve wherein the sleeve is surrounded by the outer sleeve and the outer sleeve extends axially beyond a distal end of the sleeve, and a window is arranged inside of the sleeve at the distal end.

18. A medical apparatus according to claim 1, wherein the LED illumination module is designed for application in a medical apparatus structure comprising an endoscope.

19. A medical apparatus comprising:

a light emitting diode illumination module comprising an energy source, a light emitting diode, an electrical conductor and an electrically conductive sleeve, the light emitting diode having a proximal side and a distal side, the proximal side being axially opposite the distal side with respect to a longitudinal axis of the light emitting diode illumination module, the proximal side comprising a first electrical connection contact and the distal side comprising a second electrical connection contact and a radiation region emitting radiation, the electrically conductive sleeve extending to the second electrical connection contact at the distal side from a location beyond the proximal side, wherein at least a portion of the sleeve surrounds the light-emitting diode, the sleeve comprising a radial extent and an axial extent connected to the radial extent, the radial extent extending in a radial direction with respect to a longitudinal axis of the sleeve, at least a portion of the radial extent being arranged in a light emitting area of the light emitting diode, the axial extent extending continuously at least from at least the distal side to a position located beyond the proximal side, wherein at least a portion of the axial extent is located at a radially spaced location from the light emitting diode with respect to the longitudinal axis, wherein energy is delivered from the energy source to the light emitting diode via a first electrical flow path and a second electrical flow path, the energy source, the electrically conductive sleeve and the second electrical connection contact defining at least a portion of the first electrical flow path, wherein the electrically conductive sleeve is electrically connected to the energy source and the light emitting diode, the energy source, the electrical conductor and the first electrical connection contact defining at least a portion of the second electrical flow path.

20. A medical apparatus according to claim 19, wherein the electrically conductive sleeve electrically contacts the light emitting diode, the portion of the axial extent being located radially opposite the light emitting diode with respect to the longitudinal axis, wherein the electrically conductive sleeve extends about at least a portion of the electrical conductor, the second electrical flow path being located at a spaced location from the first electrical flow path, the radiation region being located on the distal side of the light-emitting diode.

* * * * *